United States Patent [19]
Chikama

[11] Patent Number: 5,154,164
[45] Date of Patent: Oct. 13, 1992

[54] ANCHORING STRUCTURE FOR ENDOSCOPE COVER

[75] Inventor: Toshio Chikama, Tokyo, Japan

[73] Assignee: Machida Endoscope Co., Ltd., Tokyo, Japan

[21] Appl. No.: 648,834

[22] Filed: Jan. 31, 1991

[30] Foreign Application Priority Data

Feb. 1, 1990 [JP] Japan .................. 2-8122[U]

[51] Int. Cl.⁵ .......................... A61B 1/00; A61B 1/06
[52] U.S. Cl. ............................................ 128/4; 126/6
[58] Field of Search ........................................ 128/4, 6

[56] References Cited

U.S. PATENT DOCUMENTS

| | | | |
|---|---|---|---|
| 4,579,108 | 4/1986 | Bauman | 128/10 |
| 4,867,747 | 9/1989 | Yarger | 128/4 X |
| 4,869,238 | 9/1989 | Opie et al. | 128/6 |
| 4,877,033 | 10/1989 | Seitz, Jr. | 128/4 X |
| 4,881,810 | 11/1989 | Hasegawa | 128/4 X |
| 4,959,058 | 9/1990 | Michelson | 128/4 |
| 4,991,564 | 2/1991 | Takahashi et al. | 128/4 |

*Primary Examiner*—John J. Wilson
*Assistant Examiner*—Nicholas D. Lucchesi
*Attorney, Agent, or Firm*—Levisohn, Lerner & Berger

[57] ABSTRACT

An anchoring structure for an endoscope cover comprising a cylindrical rigid cover composed of an elastic material, which is fitted to an endoscope to cover a front end rigid portion of the endoscope. A transparent window is arranged on a closed face formed on the front end of the rigid cover to face at least an observation port and an illuminating port, which are arranged on the top end of the endoscope. A bag-shaped covering member having a length covering at least an intermediate conduit portion of the endoscope is attached to a rear part of the endoscope. An anchoring concave portion is formed at a predetermined part of the intermediate conduit portion, a notched face is formed on the circumferential face of the top end rigid portion and an anchoring groove is formed on the circumferential face. Anchoring projections are formed at opposite positions on the inner circumferential face of the rigid cover, and the anchoring projections are fitted in the anchoring groove of the top end rigid portion to make it possible to attach the rigid cover to the front end rigid portion. The covering member is anchored in the anchoring concave portion of the intermediate conduit portion so that the covering member can be integrated with the intermediate conduit portion.

7 Claims, 3 Drawing Sheets

ANCHORING STRUCTURE FOR ENDOSCOPE COVER

BACKGROUND OF THE INVENTION

The present device relates to an anchoring structure for a cover for covering the outer periphery of an endoscope when the endoscope is used.

After an endoscope is used in the body cavity of a patient, the endoscope is generally washed and disinfected. However, this washing and disinfecting operation requires much time and labor, and the working efficiency of the endoscope is very low. Furthermore, if this washing and disinfecting operation is not sufficiently performed, no satifactory washing and disinfecting effect can be attained.

Accordingly, an idea of a cover for covering the outer periphery of an endoscope when the endoscope is used has recently been proposed, and an example of the cover of this type is disclosed in Japanese Unexamined Patent Publication No. 61-179128.

The disclosed technique concerns an endoscope cover comprising a soft cylindrical covering member composed of a rubber or synthetic resin, which is attached to a rigid cover fitted to cover a top end rigid portion of the endoscope.

According to this endoscope cover, the rigid cover is fitted to the front end rigid portion of the endoscope, a flexible tube of the endoscope is entirely covered with the covering member from the front end side of the flexible tube. The endoscope is inserted in this state into the body cavity of a patient, and after the endoscope is used, the endoscope cover is dismounted and thrown away. When the endoscope is used again, the endoscope is covered with a new endoscope cover and is used in the above-mentioned manner. According to this technique, the endoscope need not be washed and disinfected, and a high sanitary effect is attained and the endoscope can be continuously used.

When the above-mentioned endoscope is inserted into the body cavity for the use, or is bent in the body cavity or repeatedly moved to and fro in the inserting direction, the rigid cover comes off from the front end rigid portion, or the covering member gets out of position. As the result, the intermediate conduit portion is contaminated.

It is a primary object of the present invention to protect the intermediate conduit portion of the endoscope from contamination during use and to enable the endoscope to be used immediately after a prior use.

Another object of the present invention is to provide an endoscope cover, in which, the rigid cover is prevented from being taken off or getting out of position, and complete covering of the endoscope is achieved.

Still another object of the present invention is to provide an endoscope cover, which can be taken off from the endoscope by one touch, and the removal of the used endoscope cover can be accomplished without contamination of the endoscope.

SUMMARY OF THE INVENTION

In accordance with the present device, the foregoing problems are solved by an anchoring structure for an endoscope cover comprising a cylindrical rigid cover composed of an elastic material, which is fitted to an endoscope to cover a front end rigid portion of the endoscope, a transparent window is arranged on a closed face formed on the front end of the rigid cover to face at least an observation port and an illuminating port, which are arranged on the front end of the endoscope. A bag-shaped covering member is provided having a length covering at least an intermediate conduit portion of the endoscope, which is attached to the rear part of the endoscope, wherein an anchoring concave portion is formed at a predetermined part of the intermediate conduit portion. A notched face is formed on the circumferential face of the front end rigid portion and an anchoring groove is formed on the circumferential face. Anchoring projections are formed at opposite positions on the inner circumferential face of the rigid cover and the anchoring projections are fitted in the anchoring groove of the front end rigid portion to make it possible to attach the rigid cover to the front end rigid portion, and the covering member is anchored in the anchoring concave portion of the intermediate conduit portion so that the covering member can be integrated with the intermediate conduit portion.

In the above-mentioned structure, if the rigid cover is fitted to cover the front end rigid portion of the endoscope, headed by the covering member, the anchoring projections are anchored in the groove formed in the front end rigid portion by one touch and the transparent window is positioned and fixed to face the observation port and illuminating port.

The covering member is extended along the intermediate conduit portion from the rear part to cover the intermediate conduit portion entirely. In this state, the intermediate conduit portion can be inserted into the body cavity and used for the observation without slippage or removal of the covering member. After use, the covering member is removed from the anchoring concave portion of the intermediate conduit portion and the rigid cover with the anchoring projections deformed and depressed, whereby the anchoring projections are taken off from the anchoring groove, and therefore, the rigid cover can be removed from the top end rigid portion. Moreover, by drawing out the rigid cover, the intermediate conduit portion can be drawn out from the covering member without contamination of the endoscope. Therefore, if a new endoscope cover is fitted to the endoscope, the endoscope can be directly used again.

DETAILED DESCRIPTION OF THE PREFERRED EMBODIMENTS

An example of the present device will now be described with reference to the accompanying drawings.

Figure 1:
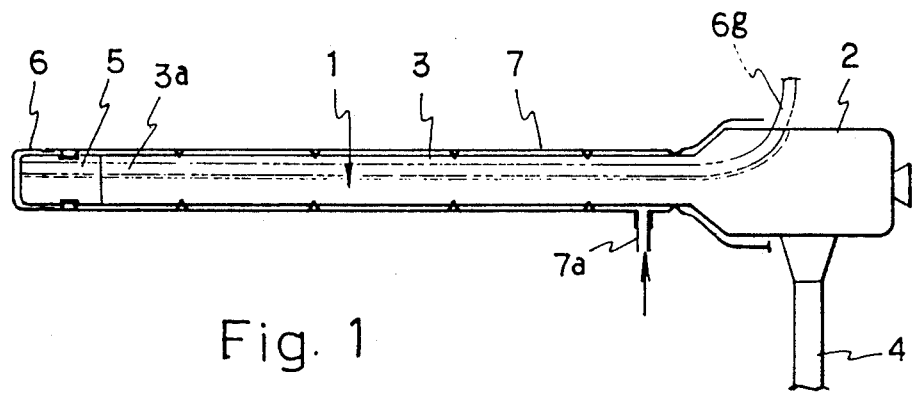
FIG. 1 is a side view illustrating the state where an endoscope cover is attached to an endoscope.
Figure 2:
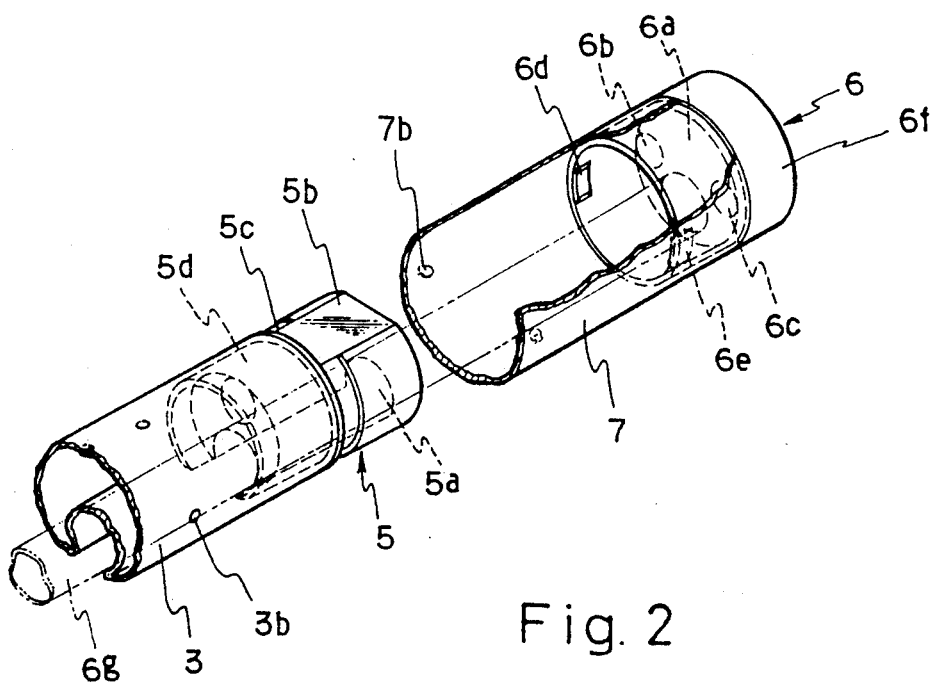
FIG. 2 is an enlarged perspective view illustrating the state of a front end rigid portion and a rigid cover in the endoscope.
Figure 3:
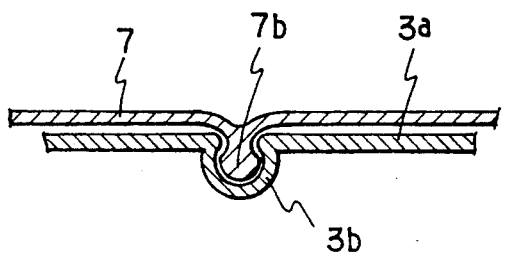
FIG. 3 is a sectional view illustrating the anchoring state of the covering member to the flexible tube portion.
Figure 4:
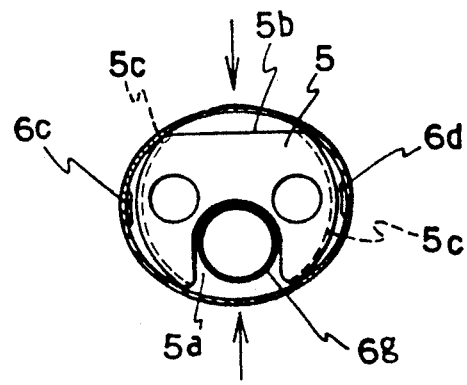
FIG. 4 is a sectional view illustrating the state where the rigid cover is taken off.
Figure 5:
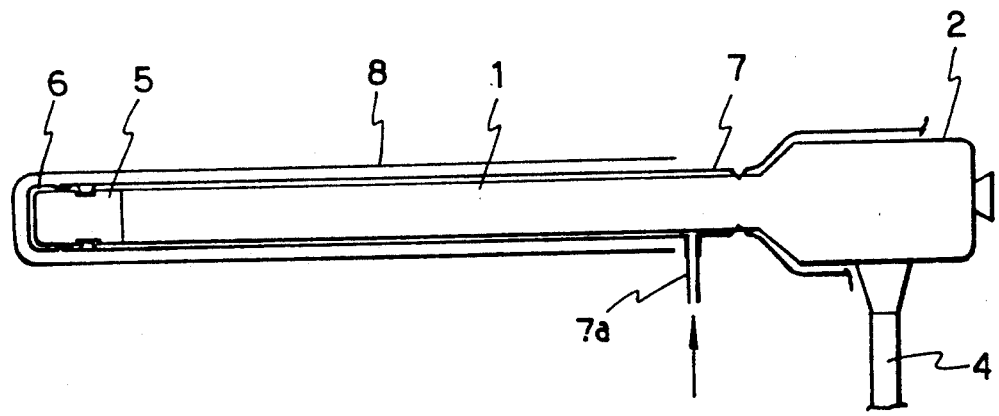
FIG. 5 is a diagram illustrating the state where the endoscope cover is taken off from the endoscope.

FIG. 1 is a side view illustrating the state where an endoscope cover is attached to an endoscope. FIG. 2 is an enlarged perspective view illustrating the state of a front end rigid portion of the endoscope and a rigid cover. FIG. 3 is a sectional diagram illustrating the anchoring state of the covering member to a flexible tube portion. FIG. 4 is a sectional view showing the state where the rigid cover is taken off. FIG. 5 is a diagram illustrating the state where the endoscope cover is taken off from the endoscope. In the drawings, reference numeral 1 represents an endoscope comprising a handle 2, an intermediate conduit portion 3 composed of a flexible tube and a guide tube portion 4 connected to a light source.

In general, an image guide, a light guide and an angle-operating wire are disposed in the intermediate conduit portion 3.

The top of the intermediate conduit portion 3 forms a bendable angle portion 3a, and around the vicinity of the base of the angle portion 3a, an anchoring concave portion 3b defined by concavities or cut grooves formed at predetermined intervals is formed. A forward end rigid portion 5 is formed on the forward end of the angle portion 3a.

An observation port connected to an image guide and an illuminating port connected to a light guide are formed in the top end of the front end rigid portion 5.

Notched faces 5a and 5b are formed on the opposite side faces of the top end rigid portion 5 by providing flatten cut on the circumference, and an anchoring groove 5c is formed on the inner curcumferential face of the forward end rigid portion 5. Reference numeral 5d represents a joint portion to the intermediate conduit portion 3. One of the notched faces 5a and 5b may act as a fitting groove in which a tube 6g having both the ends opened, such as a forceps guide tube continuous from the intermediate conduit portion 3 to the forward end rigid portion 5 or an air/water supply tube, is fitted. In the present example, this fitting groove is used.

Reference numeral 6 represents a rigid cover, which has a cylindrical shape having an inner diameter sufficient to cover the forward end rigid portion 5, and transparent windows 6b and 6c are formed on a closed face 6a at the forward end of the rigid cover 6 which faces the observation port and illuminating port, and two anchoring projections 6d and 6e are formed at cooperating positions on the inner circumferential face of the rear part. A hood 6f extended to the outer periphery of the front end can be formed according to need. If necessary, a hole corresponding to the above-mentioned fitting groove is formed on the closed face 6a and the front end portion of the tube 6g having both the ends opened, such as the forceps guide tube, is attached to this hole. Of course, this hole need not be formed in case of an endoscope not using a forceps or the like, and in this case, the above-mentioned fitting groove and the tube having both the ends opened need not be formed.

A soft bag-shaped covering member 7 formed of a rubber or synthetic resin is attached to the outer periphery of the rigid cover 6, and the diameter of the covering member 7 is almost equal to the outer diameter of the intermediate conduit portion 3 so that the covering member 7 adheres closely to the intermediate conduit portion 3. The diameter of the covering member may also be slightly larger than the outer diameter of the intermediate conduit portion 3 so that the covering member 7 loosely covers the intermediate conduit portion 3. In each case, the end portion of the covering member 7 adheres and anchors closely to the intermediate conduit portion 3 at the position of the root of the handle 2 or covers the handle 2 entirely. At the rear portion of the covering member 7, an air-injecting opening 7a is formed so that air can be injected into the covering member 7 from this air-injecting opening 7a.

Anchoring convexities 7b to be engaged with the above-mentioned anchoring concavities 3b are attached at the same intervals as those of the anchoring concavities 3b on the inner side of the portion from the front end of the covering member 7 to the vicinity of the base of the above-mentioned angle portion 3a.

In the above-mentioned example, two notched faces or the fitting groove and notched face are formed, but if the rigid cover is deformed and the anchoring projection is taken off from the anchoring groove, one notched face suffices.

In the example having the above-mentioned structure, if the rigid cover 6, headed by the covering member 7, is fitted to cover the front end rigid portion 5 of the endoscope, the anchoring projections 6d and 6e are anchored to the anchoring groove 5c of the front end rigid portion 5 by one touch because of the elasticity of the rigid cover 6 and the holes 6b and 6c which are positioned and fixed to face the observation port and illuminating port.

Then, the covering member 7 is extended from the rear part along the intermediate conduit portion 3 to cover the intermediate conduit portion 3 entirely or to cover even the handle 2 as well as the intermediate conduit portion 3. In this case, the anchoring convexities 7b of the covering member 7 are engaged with the anchoring concavities 3b of the intermediate conduit portion 3 to integrate the covering member 7 with the intermediate conduit portion 3. In this state, the intermediate conduit portion 3 is inserted into the body cavity and is used for the observation.

After the observation, the endoscope cover is taken out from the endoscope. At first the rigid cover 6 is depressed from the outside at positions separated by 90° from the positions of the anchoring projections 6d and 6e (these positions are preferably marked), that is, at the corresponding positions of the notched faces 5a and 5b of the front end rigid portion 5, as shown in FIG. 4, whereby the rigid cover 6 is deformed and expanded and the anchoring projections 6d and 6e are removed from the anchoring groove 5c. In this state, the rigid cover 6 can be removed from the top end rigid portion 5 by pulling. These procedures will now be described in due order.

As shown in FIG. 5, the endoscope is put into a transparent bag 8 having a length sufficient to contain the entire endoscope therein or contain at least the entire intermediate conduit portion 3 therein, so that the operation is carried out in the state where the endoscope is grasped through the bag 8.

At first, air is injected into the covering member 7 from the air-injecting opening 7a to separate the endoscope cover from the endoscope, and the anchoring convexities 7b of the covering member 7 are taken out from the anchoring concavities 3b of the intermediate conduit portion 3 to separate the covering member 7 from the intermediate conduit portion 3. Then, the rigid cover 6 is depressed from the outside at positions separated by 90° from the positions of the anchoring projections 6d and 6e, whereby the rigid cover 6 is deformed and the anchoring projections 6d and 6e are taken off from the anchoring groove 5c. Therefore, the rigid cover 6 can be taken out from the front end rigid portion 5 and the intermediate conduit portion 3 can be drawn out from the endoscope cover by pulling it together with the bag 8. The endoscope cover is thrown away together with the bag 8, and the endoscope is not contaminated.

Accordingly, by attaching a new endoscope cover to the endoscope, the endoscope can be immediately used again.

Figure 6:
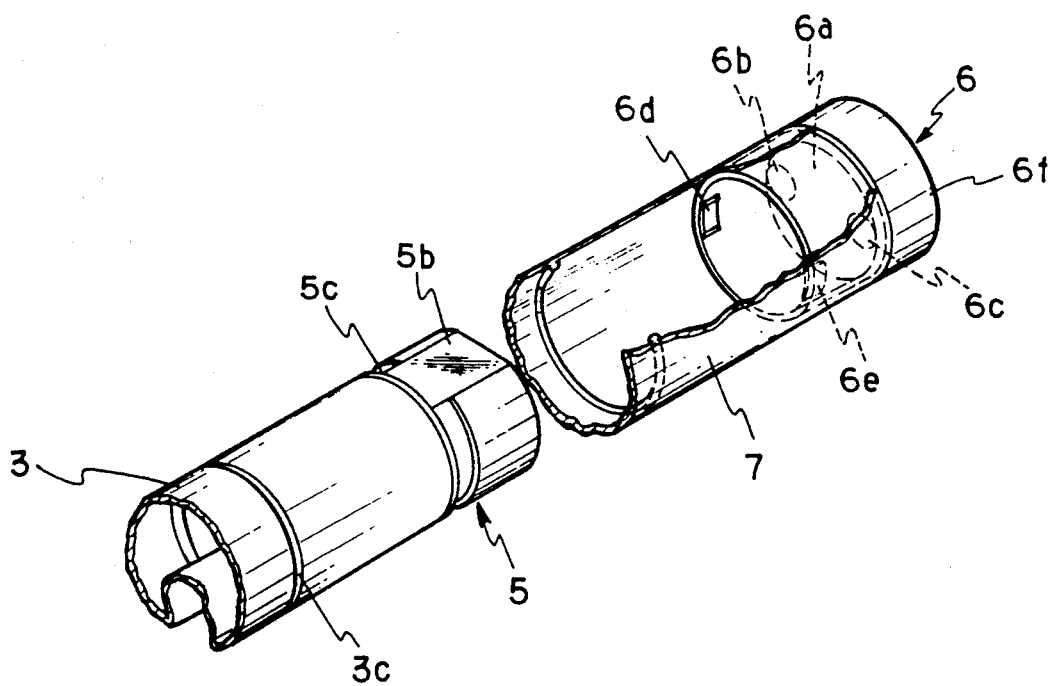
FIG. 6 is a diagram illustrating a second example of this invention.

In the foregoing example, the anchoring concave portion 3b is defined by concavities or cut grooves formed at predetermined intervals, and the concave portion may be a continous cut groove 3c, as shown in FIG. 6. In this case, there can be adopted a method in which the anchoring convex portion is not formed but a part of the endoscope cover is pressed into the cut groove 3c to anchor the endoscope cover.

The position of the anchoring concave portion 3b or the cut groove 3c is not limited to the vicinity of the base of the angle portion 3a, and the anchoring concave portion 3b or cut groove 3 may be formed at a plurality of positions.

Figure 7:
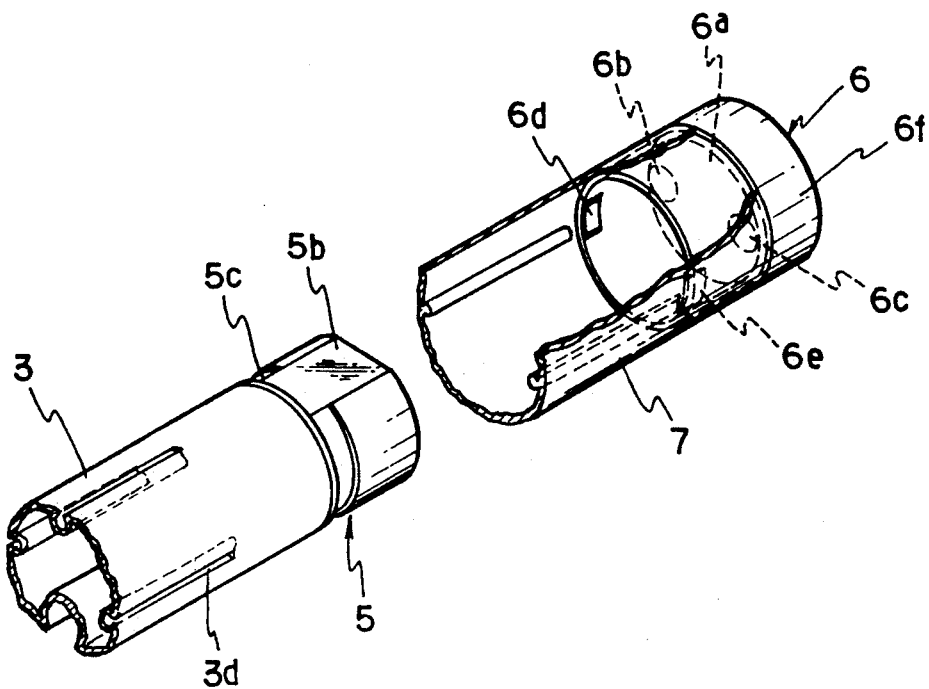
FIG. 7 is a diagram illustrating a third embodiment of this invention.

Furthermore, there can be adopted a modification in which, as shown in FIG. 7, at least one cut groove 3d is formed along the longitudinal direction of the intermediate conduit portion 3, and the endoscope cover is pressed into the cut groove 3d to anchor the endoscope cover. In this modification, an anchoring ring or the like may be disposed to anchor the endoscope cover in the cut groove 3d.

As is apparent from the foregoing detailed description, according to the present device, there is provided an anchoring structure for an endoscope cover comprising a cylindrical rigid cover composed of an elastic material, which is fitted to an endoscope to cover a front end rigid portion of the endoscope, a transparent window arranged on a closed face formed on the top end of the rigid cover which faces at least an observation port and an illuminating port, which are arranged on the top end of the endoscope. A bag-shaped covering member is provided having a length covering at least an intermediate conduit portion of the endoscope, which is attached to the rear part of the endoscope, wherein an anchoring concave portion is formed at a predetermined part of the intermediate conduit portion, a notched face is formed on the circumferential face of the front end rigid portion and an anchoring groove is formed on the circumferential face, anchoring projections are formed at facing positions on the inner circumferential face of the rigid cover and the anchoring projections are fitted in the anchoring groove of the top end rigid portion to make it possible to fix the rigid cover to the top end rigid portion, and the covering member is anchored in the anchoring concave portion of the intermediate conduit portion so that the covering member can be integrated with the intermediate conduit portion. In this structure, even if the endoscope is used, for example, in the body cavity, since the intermediate conduit portion, that is, the inserting portion, is covered with the covering member, the endoscope is not contaminated, and only by exchanging the endoscope cover with a new endoscope cover after the use, the endoscope can be immediately used again.

Moreover, since the rigid cover can be fixed to the front end rigid portion, the rigid cover is prevented from being taken off or moving out of position, and complete of the endoscope with the cover is ensured.

Moreover, since the endoscope cover can be removed from the endoscope by one touch, the removal of the used endoscope cover can be accomplished without contamination of the endoscope. This is another effect attained by the present device.

What is claimed is:

1. In combination, an endoscope, an endoscope cover and anchoring structure comprising a cylindrical rigid cover composed of an elastic material, which is fitted to said endoscope to cover a front end rigid portion of the endoscope, the endoscope having a rear part, the cover having a transparent window arranged on a closed face formed on the front end of the rigid cover which faces at least an observation port and an illuminating port of the endoscope, said transparent window facing the front end of the endoscope, the cover also having a bag-shaped covering member having a length covering at least an intermediate conduit portion of the endoscope, which is attached to the rear part of the endoscope, an anchoring concave portion is formed on the intermediate conduit portion, said front end rigid portion having a cylindrical structure, a notched face is formed on an outer circumferential face of the cylindrical structure of the front end rigid portion and an anchoring groove is also formed on said circumferential face, anchoring projections are formed at opposite sides on an inner circumferential face of the rigid cover, said anchoring projections being fitted in the anchoring groove of the front end rigid portion to attach the rigid cover to the front end rigid portion, said covering member also being anchored in the anchoring concave portion of the intermediate conduit portion so that the covering member can be integrated with the intermediate conduit portion.

2. The combination according to claim 1, wherein the anchoring concave portion is a cut groove.

3. The combination according to claim 1, wherein the anchoring concave portion is formed in the circumferential direction of the intermediate conduit portion.

4. The combination according to claim 3, wherein the anchoring concave portion is a cut groove.

5. The combination according to claim 1, wherein the anchoring concave portion is formed in the longitudinal direction of the intermediate conduit portion.

6. The combination according to claim 5, wherein the anchoring concave portion is a cut groove.

7. The combination according to claim 1, wherein an air-injecting opening is formed at the rear end of the covering member.

* * * * *